United States Patent
Hamernik et al.

(10) Patent No.: US 8,550,113 B1
(45) Date of Patent: Oct. 8, 2013

(54) VACUUM BREAKER FLOW REGULATOR

(75) Inventors: Edward L. Hamernik, Fridley, MN (US); David B. Larson, Maple Grove, MN (US)

(73) Assignee: Hamernik-Harrod, Inc., Blaine, MN (US)

( * ) Notice: Subject to any disclaimer, the term of this patent is extended or adjusted under 35 U.S.C. 154(b) by 422 days.

(21) Appl. No.: 12/798,266

(22) Filed: Mar. 31, 2010

Related U.S. Application Data

(60) Provisional application No. 61/211,866, filed on Apr. 3, 2009.

(51) Int. Cl.
*F16K 31/12* (2006.01)

(52) U.S. Cl.
USPC ...... 137/505.18; 137/510; 251/229; 251/231; 251/282; 251/263

(58) Field of Classification Search
USPC ............. 137/494, 509, 510, 505.18; 251/229, 251/231, 251, 282, 263, 242–246
See application file for complete search history.

(56) References Cited

U.S. PATENT DOCUMENTS

| | | | |
|---|---|---|---|
| 2,702,561 A * | 2/1955 | Geffroy | 137/98 |
| 2,772,067 A * | 11/1956 | Wilson | 251/229 |
| 2,988,097 A * | 6/1961 | Benzel | 137/494 |
| 3,272,143 A * | 9/1966 | Rice | 417/569 |
| 5,665,894 A | 9/1997 | Baker | |
| 5,931,188 A * | 8/1999 | Sprague | 137/505.18 |
| 6,776,388 B2 * | 8/2004 | Baumann | 251/61.4 |
| 7,658,366 B2 * | 2/2010 | Larsen | 251/282 |
| 2002/0066481 A1 * | 6/2002 | Oestreich et al. | 137/82 |
| 2003/0066562 A1 * | 4/2003 | Wakeman | 137/505 |
| 2004/0055646 A1 * | 3/2004 | Robinson et al. | 137/510 |
| 2009/0301581 A1 * | 12/2009 | MacNeal et al. | 137/505.14 |

FOREIGN PATENT DOCUMENTS

WO    WO 2008146038 A1 * 12/2008

\* cited by examiner

*Primary Examiner* — Craig Schneider
*Assistant Examiner* — Jessica Cahill
(74) *Attorney, Agent, or Firm* — Emch, Schaffer, Schaub & Porcello Co. LPA

(57) ABSTRACT

A single stage vacuum breaker flow regulator includes a diaphragm retained in an elevated position in between atmosphere and an outlet chamber for a gaseous medium. A valve in communication with an inlet chamber is yieldingly urged to a closed position by a spring. Cam levers are movable by the diaphragm upon a reduction in pressure to sub-atmospheric in the outlet chamber. The movement of said cam levers in response to a reduction in pressure is transmitted to a yieldingly movable valve to open said valve to the flow of gas from said inlet chamber to said outlet chamber.

25 Claims, 4 Drawing Sheets

VACUUM BREAKER FLOW REGULATOR

CROSS REFERENCE TO RELATED APPLICATION

This application is based upon and claims the benefit of U.S. Provisional Patent Application No. 61/211,866 filed Apr. 3, 2009.

BACKGROUND OF THE INVENTION

Gas flow regulators for medical, instrumentation and other purposes come in a number of different varieties. One such type of gas flow regulator is known as a demand flow regulator, one model of which is described in U.S. Pat. No. 5,665,894. The gas flow regulator disclosed in U.S. Pat. No. 5,665,894 is a two stage regulator.

SUMMARY OF THE INVENTION

The present invention is directed to a single stage vacuum breaker flow regulator. It is a low cost, highly accurate device which can be precisely set or adjusted to suit the desired actuation pressure and flow desired by the user. This is accomplished through the use of a balanced valve poppet that is able to supply gas from a positive source as needed into a sub-atmospheric chamber as required by the process or instrument.

Objects and advantages of the present invention will become apparent to those skilled in the art upon a review of the following detailed description of the preferred embodiments and the accompanying drawings.

IN THE DRAWINGS

DETAILED DESCRIPTION OF THE INVENTION

Figure 1:
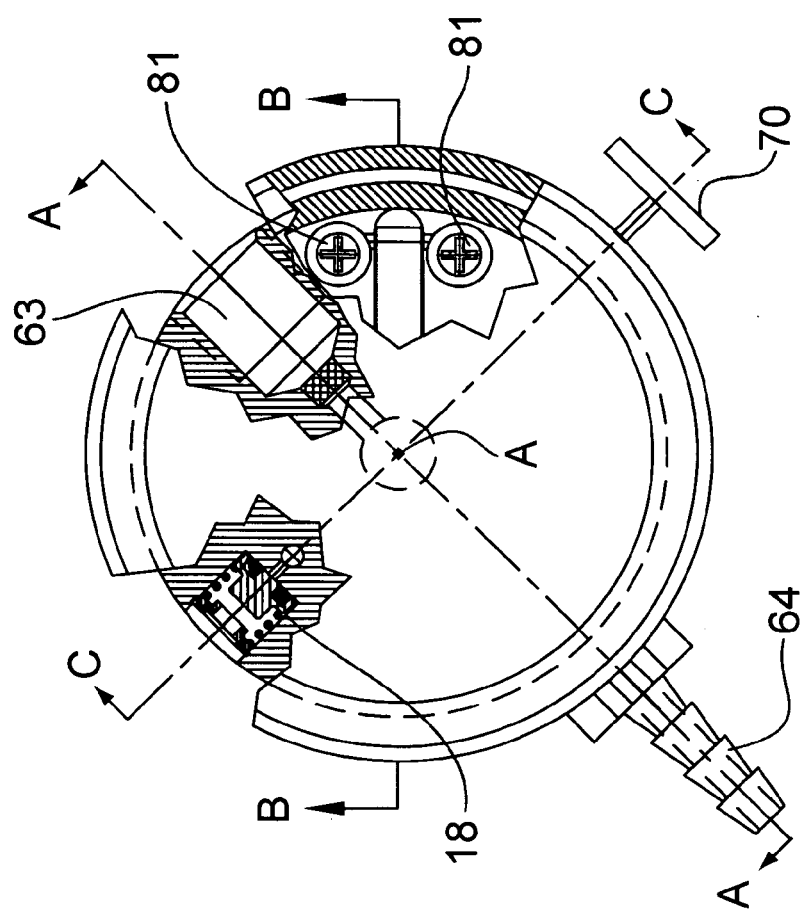
FIG. 1 is a top plan view of the regulator of the present invention.

Referring to the drawings there is shown a single stage vacuum breaker flow regulator 10.

The vacuum breaker flow regulator 10 includes a body 12 with an inlet 63, a barb-hose type outlet 64 and a chamber 30 which extends along axis A upwardly from the lower surface 16 of the body 12. A pressure gauge 70 is mounted on the body 12 in an area approximately 90° from each of the inlet 63 and outlet 64 and communicates with the chamber 30 by means of lateral passageway 72. A safety relief 18 is mounted on the body 12 in an area generally opposite the pressure gauge 70. The safety relief is one of standard type in the field of gas flow regulators and does not need further description. The inlet 63 includes a reduced size passageway 65 extending to the chamber 30.

Positioned in the chamber 30 is a balanced poppet valve 19 extending from a reduced size lower extension 19A to an enlarged upper flange 19B having a radially extending shoulder 19C at the lower end thereof. A central section 19D extends between the lower extension 19A and the radially extending shoulder 19C and is spaced from the sidewall of chamber 30. Additionally, the enlarged upper flange 19B has at least one area in its outer periphery, such as a flat panel for example, which is spaced from the sidewall of the chamber 30 in order to permit the flow of gas therearound when the valve is open. Balancing the poppet valve reduces the effect of changing inlet pressure on the cracking pressure of the regulator.

Encircling the poppet valve extension 19A and a major portion of the central section 19D of the poppet valve 19 is a valve housing 20 having a lower axial passageway 22 in which the lower poppet valve extension 19A is slidably positioned. The lower axial passageway 22 and, therefore, the end of the reduced size lower extension 19A are at atmospheric pressure. The valve housing 20 is positioned in the lower area of body chamber 30 and has a lower chamber 24 in which is positioned a Teflon® back-up ring 26 and an O-ring seal 28 effecting a seal between the chamber 24 and the poppet valve extension 19A. Above the reduced size lower chamber 24 of the valve housing 20 is an enlarged upper chamber 31. A valve guide 32 is positioned in the upper chamber 31 and has a lower reduced size portion 32A which extends into the reduced size lower chamber 24. A compression spring 34 is positioned in the upper chamber 31 and its lower end rests against the valve guide 32. The compression spring 34 extends out of the valve housing 20, into the body chamber 30 where its upper end engages the radially extending shoulder 19C to yieldingly urge the poppet valve 19 to a sealed position.

The regulator body 12 has an upper passageway 38 permitting the flow of fluid to and from the chamber 30. The upper passageway 38 is the same diameter as the lower axial passageway 22 of the valve housing 20. A Teflon® seal 36 is positioned at the upper end of the poppet valve 19 and has an outwardly convexed sealing surface 36A which engages and effects a seal of said upper passageway 38. A stainless steel collar 40 encircles a reduced size upper portion of the Teflon® seal 36 to support it in the recess of the enlarged upper portion 19B of the poppet valve 19.

The upper surface 30A of the chamber 30 tapers downwardly in a direction toward axis A in order to permit the convex upper surface 36A of the Teflon® seal 36 to effect a sound seal to close the passageway 38 when so desired. Connected to and extending from the Teflon® seal 36 is an actuator pin 44 having a lower cylindrical portion which extends through passageway 38 outwardly from the fluorocarbon seal 36 along axis A. The actuator pin 44 extends from its lower cylindrical portion received in the Teflon® seal 36 to a conical portion 44A from which extends a hexagonal head portion 44B. The conical portion 44A and enlarged hexagonal head portion 44B are positioned in a cylindrical outlet chamber 46 at the upper end of the body 12. As a result of the actuator pin hexagonally shaped head portion 44B being positioned in a chamber 46 which is cylindrical in shape, flow passages are provided between the hex flats of the enlarged head 44B and the cylindrical wall of the chamber 46. Additionally, the lower cylindrical portion of the actuator pin 44 is smaller in diameter than passageway 38 thereby permitting gas to flow through passageway 38 around the outside of the lower cylindrical portion. This coupled with the equal areas of the lower axial passageway 22 (with stem 19A, seal 28 and backup ring 32A) and the upper axial passageway 38 (with seat 36) provides a balancing effect of the forces on the poppet valve 19. This balancing of areas negate the effect of changing inlet pressures on the sensitivity and cracking pressure of the regulator and reduces the force required to open the valve.

The upper end of the body 12 has an upper surface 12A and a substantially cylindrical wall 128 extending upwardly therefrom. The cylindrical wall 128 terminates in a radially outwardly extending flange 12C. The flange 12C defines a circle and serves to support the outer edge of a deformable diaphragm 50 and bonnet 52. The diaphragm 50 includes an upper elastomer sheet 50A adhered to a thin stainless metal disk 50B. The metal disk provides rigidity to the center portion of the diaphragm so that as the diaphragm is moved downward, the diaphragm deformation takes place in the edge convolution 50D. The bonnet 52 has, at its outer periphery, a downwardly extending U-shaped portion 52A which engages the outer periphery of the diaphragm 50. An upwardly extending collar 12D is formed inwardly to clamp the bonnet 52 and the diaphragm 50 to the radial flange 12O of the housing 12 and form a diaphragm seal.

Figure 2:
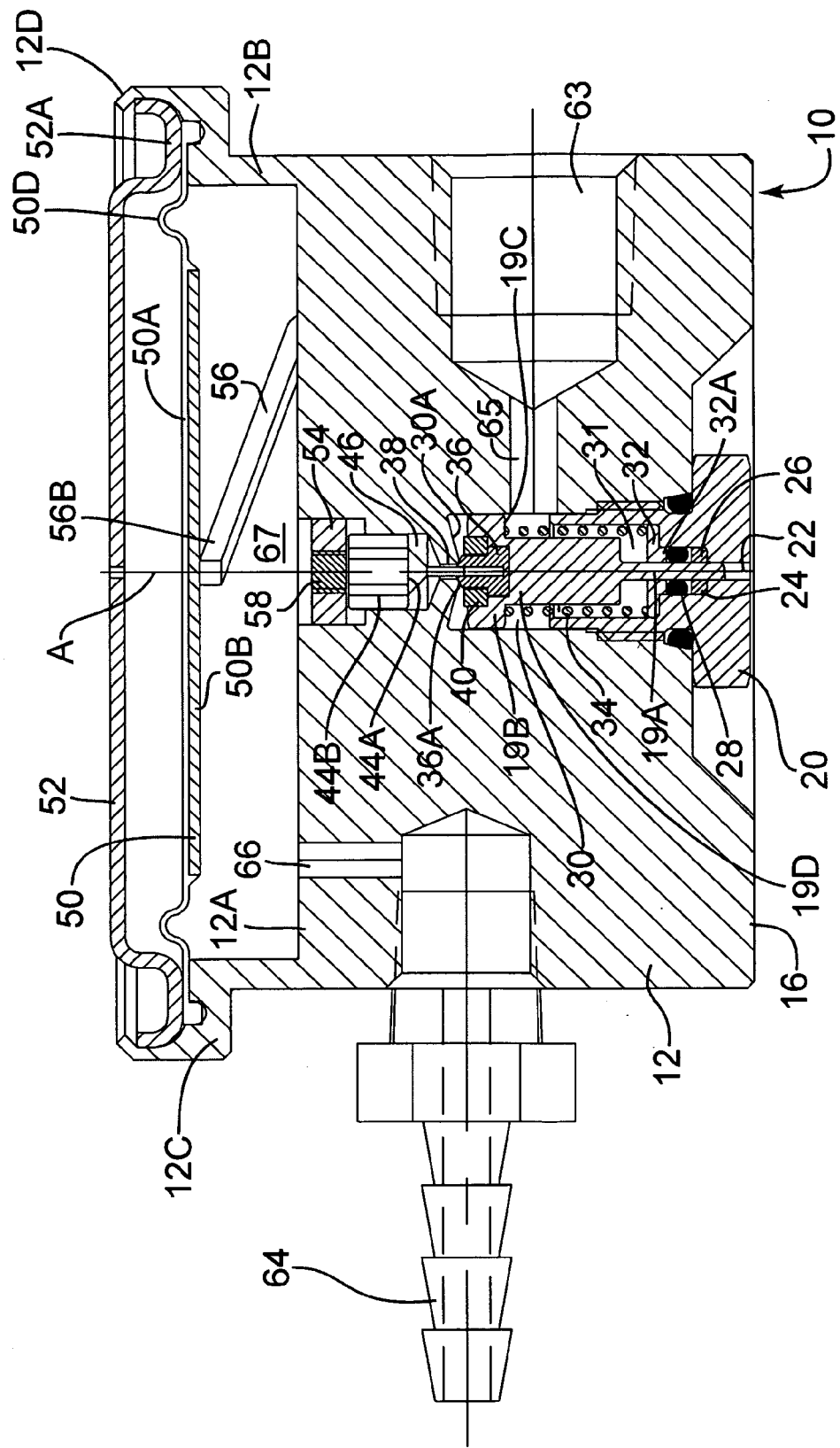
FIG. 2 is an enlarged sectional view taken along line A-A of FIG. 1.
Figure 3:
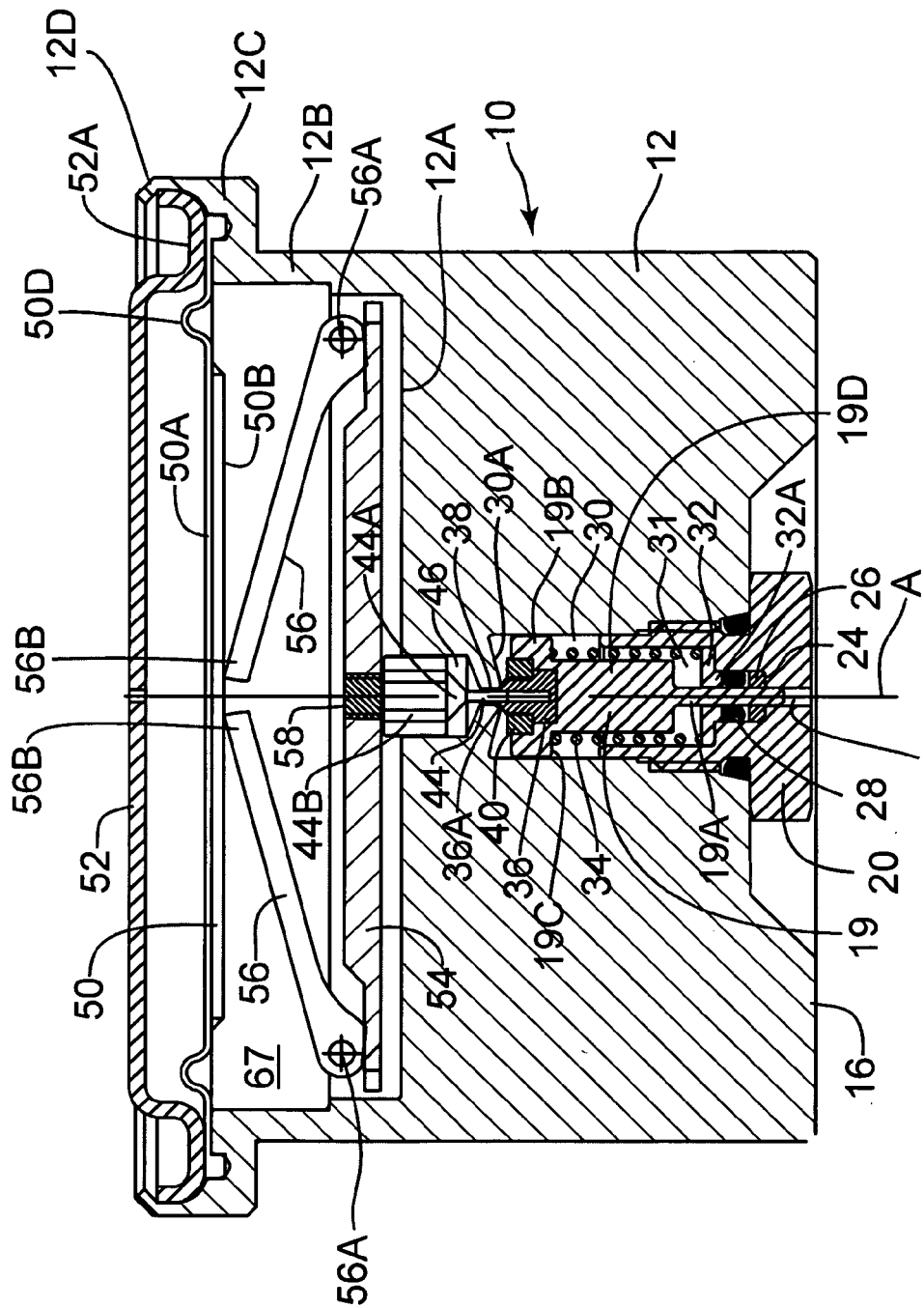
FIG. 3 is an enlarged sectional view taken along line B-B of FIG. 1.
Figure 4:
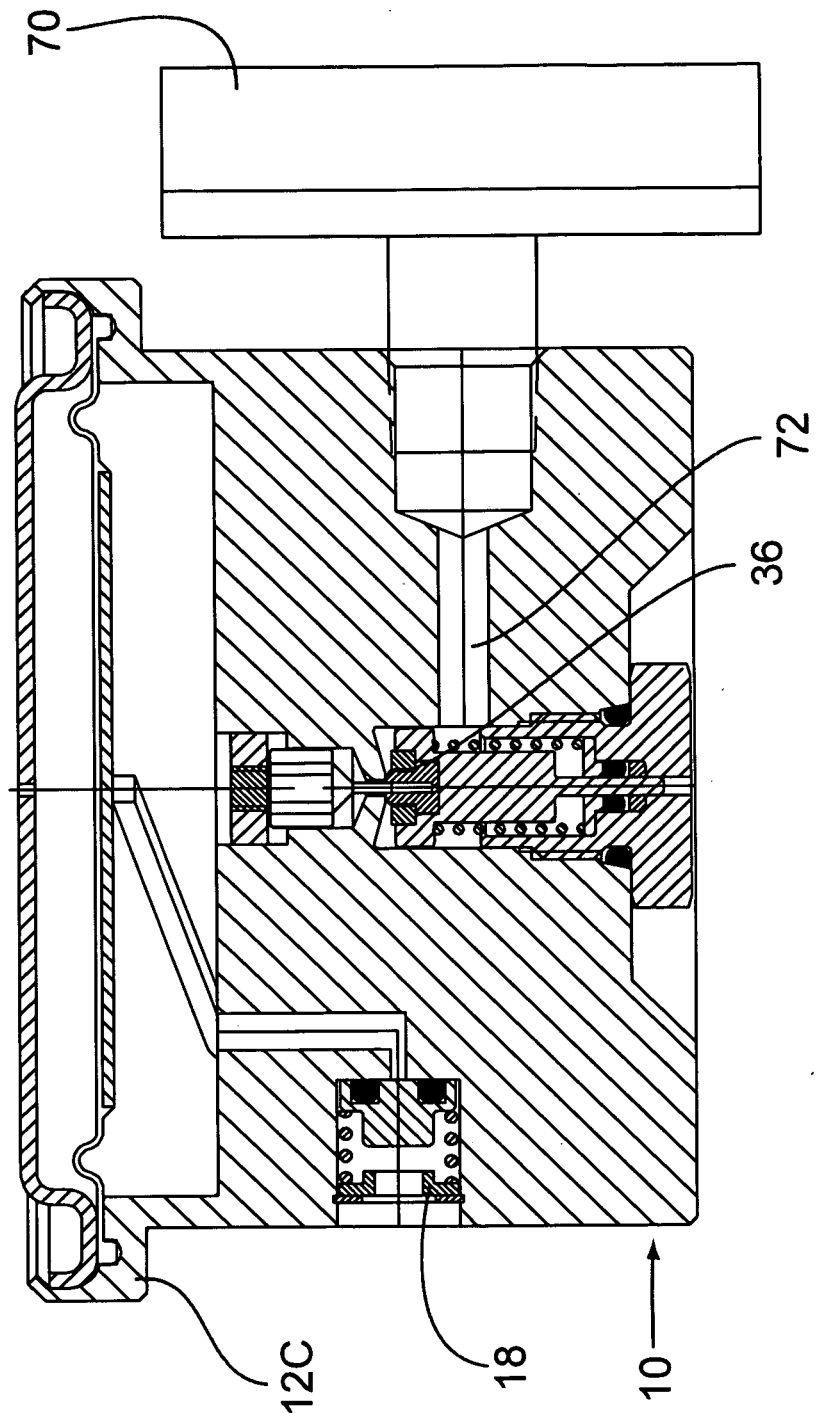
FIG. 4 is a sectional view taken through line C-C of FIG. 1.

Positioned in the space 67 between the diaphragm 50 and the upper surface 12A of the body 12 is a loading lever 54 formed of stainless steel. The loading lever 54 has a thickness on the order of 0.090 inch which is sufficient to provide significant rigidity to the loading lever to permit it to act upon the poppet valve to move the poppet valve 19 to an open position when the loading lever is caused to move downwardly as hereinafter described. A pair of cam levers 56 are pivotally supported in the space 67 between the diaphragm 50 and the loading lever 54 by means of a pin extending through an aperture 56A of each cam lever. Screws 81 engage and hold in position opposing ends of each pin extending outwardly from the aperture 56A of each cam lever. The cam levers 56 are resiliently urged to an angle upwardly into contact with the metal member 50B of the diaphragm 50 by means of upward urging of the loading lever 54 by the spring 34. Threadedly engaged to the loading lever 54 is an adjusting screw 58. The adjusting screw 58 can be rotated to move the loading lever 54 and the pivoted ends 56A of the cam levers 56 to thereby precisely set the regulator to a position for opening the poppet valve 19 at the precise amount of pressure as demanded by instrumentation attached to the outlet 64 of the regulator as shown in FIGS. 1 and 2. Rotation of the adjusting screw 58 moves the loading lever 54 and the cam levers 56 to a position at which the free ends 56B touch the stainless metal disk 50B of the diaphragm 50 but do not put any significant force on it.

Upon a reduction in pressure in the space 67 occupied by the cam levers 56 as a result of the demand for gas from an outside source, the diaphragm 50 will be sucked downwardly thereby pushing the free ends 56B of the cam levers 56 into engagement with the loading lever 54 and its adjusting screw 58 to thereby push the loading lever 54 and screw 58 downwardly to a position at which they engage the upper end of the hexagonally shaped portion 44B of the actuator pin 44. Continued movement downwardly moves the poppet valve 19 downwardly against the resilience of spring 34 to disengage the Teflon® seal 36 from the upper surface 30A of the chamber 30, and thereby opening the passageway 38 to permit the flow of gas. The metal member 50B protects the elastomer sheet 50A from being damaged by the cam levers 56.

The demand for gas by outside instrumentation connected to the outlet 64 communicating with the space 67 below the flexible diaphragm 50 by means of passageway 66 creates a partial vacuum which causes the flexible diaphragm 50 to be drawn downwardly carrying with it the cam levers 56, the free ends of which then contact the loading lever 54 pushing it and adjusting screw 58 downwardly to a position contacting the enlarged head of the actuator pin 44. Continued downward movement of the loading lever 54 causes the Teflon® seal 36 to move downwardly out of engagement with upper surface 30A thereby opening the passageway 38 to the flow of gas to the outside instrumentation through outlet 64. As previously noted adjustment of the screw 58 permits precise adjustment of pressure and the flow of gas.

The diaphragm 50 acts as a sensing element to control, the movement of the fluorocarbon 36 and, thereby, the opening and closing of the passageway 38. By virtue of the diaphragm 50, the regulator of the present invention has a sensitivity such that it can be opened at a much lower pressure (crack pressure) than prior art vacuum breaker/demand flow regulators. Thus, the regulator of the present invention can be opened at a vacuum pressure of 1.5 inches of water pressure (005 psig) as compared with prior art demand regulators which require crack pressures of 3 inches of water pressure or more. This degree of sensitivity, coupled with the feature of the adjusting screw 58 provides a vacuum breaker/demand flow regulator with greater sensitivity than similar types of prior art regulators. A significant feature of the present invention is the balancing effect resulting from equal areas of the poppet valve extension 19A and seals in lower axial passageway 22 of the valve housing 20 and the sealing area created by the seal 36 sealing upper passageway 38.

The above detailed description of the present invention is given for explanatory purposes. It will be apparent to those skilled in the art that numerous changes and modifications can be made without departing from the scope of the invention. Accordingly, the whole of the foregoing description is to be construed in an illustrative and not a limitative sense, the scope of the invention being defined solely by the appended claims.

The invention claimed is:

1. A single stage regulator for the flow of gas comprising:
   (a) a body having an inlet, an outlet and a valve between said inlet and said outlet, said valve yieldingly movable along an axis from a closed position to an open position;
   (b) a compartment space between said valve and said outlet positioned to receive gas flowing through said valve when said valve is open, said compartment space communicating with said outlet;
   (c) a diaphragm on the opposite side of said compartment space from said valve, said diaphragm movable in response to a reduction in pressure in said compartment space to reduce the size of said compartment space;
   (d) one or more cam members engaged to said diaphragm and movable in response to movement of said diaphragm, movement of said cam members in response to a reduction in pressure causing axial movement of said valve to an open position permitting flow of gas from said inlet, to said compartment space and to said outlet;
   (e) an axially extending opening including (i) a first chamber housing said valve for receiving gas from said inlet, (ii) a second chamber between said first chamber and said diaphragm and (iii) a first passageway between said first chamber and said second chamber, said first passageway being smaller in size than both said first chamber and said second chamber;
   (f) a seal mounted on said valve for closing said first passageway;
   (g) a valve housing axially spaced from said seal encircling a portion of said valve, said valve housing having an axial passageway between said first chamber and atmosphere, said axial passageway being sealed with seal rings is substantially the same area as said first passageway, said valve including reduced size extension slidably engaged in said axial passageway, and
   (h) a spring yieldingly urging said valve axially to a position at which said seal closes the passageway between said first chamber and said second chamber.

2. A single stage regulator for the flow of gas comprising:
   (a) a body having an axial opening extending along an axis from a lower end to an upper end, an inlet disposed at an angle to said axis extending to said axial opening, an outlet and a valve between said inlet and said outlet, said valve yieldingly movable along said axis from a closed position to an open position, said axial opening including (i) a first chamber housing said valve for receiving gas from said inlet, (ii) a second chamber between said first chamber and said upper end and (iii) a first passageway between said first chamber and said second chamber, said first passageway being smaller in size than both said first chamber and said second chamber;

(b) a compartment space between said valve and said outlet positioned to receive gas flowing through said valve when said valve is open, said compartment space communicating with said outlet;

(c) a diaphragm on the opposite side of said compartment space from said valve, said diaphragm movable in response to a reduction in pressure in said compartment space to reduce the size of said compartment space;

(d) one or more cam members engaged to said diaphragm and movable in response to movement of said diaphragm, movement of said cam members in response to a reduction in pressure causing axial movement of said valve to an open position permitting flow of gas from said inlet, to said compartment space and to said outlet;

(e) a seal mounted on said valve for closing said first passageway;

(f) a valve housing axially spaced from said seal encircling a portion of said valve, said valve housing having an axial passageway between said first chamber and atmosphere, said axial passageway being substantially the same size as said first passageway, said valve including reduced size extension slidably engaged in said axial passageway;

(g) a spring yieldingly urging said valve axially to a position at which said seal closes the passageway between said first chamber and said second chamber;

(h) a valve guide positioned in said valve housing and encircling said valve extension;

(i) an actuator pin contacting said valve seal, said actuator pin movable axially in response to movement of said cam members to move said seal and said valve to open said passageway to the flow of gas;

(j) an adjustment member on said actuator pin for varying the amount of travel required to move said actuator pin and valve; and (k) a loading lever in contact with said actuator pin, said loading lever being movable by said one or more cam members to move said valve to said open position.

3. The single stage regulator according to claim 2 wherein said diaphragm includes a flexible elastomeric member and a metal plate engaged thereto, said metal plate being positioned to be contacted by said one or more cam members, said cam members sliding against said plate in response to movement of said diaphragm.

4. The single stage regulator according to claim 2 wherein said body upper end has an elongated recess passing through said axis, said loading lever being positioned in said recess and two of said cam members are pivotally mounted in opposite ends of said recess and are engaged at said ends by said loading lever.

5. A single stage regulator for the flow of gas comprising:
(a) a body having an inlet, an outlet and a valve between said inlet and said outlet, said valve yieldingly movable along an axis from a closed position to an open position wherein said body has an axially extending opening including (i) a first chamber housing said valve for receiving gas from said inlet, (ii) a second chamber between said first chamber and said diaphragm and (iii) a first passageway between said first chamber and said second chamber, said first passageway being smaller in size than both said first chamber and said second chamber;

(b) a compartment space between said valve and said outlet positioned to receive gas flowing through said valve when said valve is open, said compartment space directing the flow of gas to said outlet;

(c) a diaphragm on the opposite side of said compartment space from said valve, said diaphragm movable in response to a reduction in pressure in said compartment space to reduce the size of said compartment space;

(d) one or more cam members engaged to said diaphragm and movable in response to movement of said diaphragm, movement of said cam members in response to a reduction in pressure causing axial movement of said valve to an open position permitting flow of gas from said inlet, to said compartment space and to said outlet (e) a seal mounted on said valve for closing said first passageway;

(f) a valve housing axillary spaced from said seal encircling a portion of said valve, said valve housing having an axial passageway between said first chamber and atmosphere, said axial passageway being sealed with seal rings is substantially the same area as said first passageway, said valve including reduced size extension slidably engaged in said axial passageway, and (g) a spring yieldingly urging said valve axially to a position at which said seal closes the passageway between said first chamber and said second chamber.

6. The single stage regulator according to claim 5 further including a valve guide positioned in said valve housing and encircling said valve extension.

7. The single stage regulator according to claim 5 wherein said diaphragm includes a flexible elastomeric member and a metal plate engaged thereto, said metal plate being positioned to be contacted by said one or more cam members, said cam members sliding against said plate in response to movement of said diaphragm, said diaphragm has a convolution between the metal plate and a body flange where diaphragm movement takes place allowing diaphragm movement with minimum resistance.

8. The single stage regulator according to claim 5 wherein each said cam member has a first end engaged to said diaphragm and a second end, a pivot pin adjacent said second end defining an axis about which said cam member can rotate upon movement of said diaphragm.

9. The single stage regulator according to claim 8 wherein each said pivot pin includes screws or other retainer members for holding said cam members position for rotational movement about said axis.

10. The single stage regulator according to claim 5 wherein each said cam member has a first end engaged to said diaphragm and a second end, a pivot pin adjacent said second end defining an axis about which said cam member can rotate upon movement of said diaphragm.

11. The single stage regulator according to claim 10 wherein each said pivot pin includes screws or other retainer members for holding said cam members in position for rotational movement about said axis.

12. The single stage regulator according to claim 10 wherein said cam members are urged into engagement with said diaphragm by said spring.

13. The single stage regulator according to claim 5 further including an actuator pin contacting said valve seal, said actuator pin movable axially in response to movement of said one or more cam members to move said seal and said valve to open said first passageway to the flow of gas.

14. The single stage regulator according to claim 13 further including an adjustment member on said actuator pin for varying the amount of diaphragm travel required to move said actuator pin and valve.

15. The single stage regulator according to claim 13 wherein said body has an end spaced from and facing said diaphragm, said end defining one side of said compartment space and having an elongated recess passing through said axis and overlying said valve and further including a loading lever positioned in said recess in contact with said actuator pin, said loading lever being movable by said one or more cam members to move said valve to said open position.

16. The single stage regulator according to claim 15 further including an adjustment member threadably engaged to said loading lever to vary the amount of diaphragm travel required to move said actuator pin.

17. The single stage regulator according to claim 15 wherein two cam members are pivotally mounted in opposite ends of said recess and are engaged at said ends by said loading lever.

18. A single stage regulator for the flow of gas comprising:
 (a) a body having an axial opening extending along an axis from a lower end to an upper end, an inlet disposed at an angle to said axis extending to said axial opening, an outlet and a valve between said inlet and said outlet, said valve yieldingly movable along said axis from a closed position to an open position, said axial opening including (i) a first chamber housing said valve for receiving gas from said inlet, (ii) a second chamber between said first chamber and said upper end and (iii) a first passageway between said first chamber and said second chamber, said first passageway being smaller in size than both said first chamber and said second chamber;
 (b) a compartment space between said valve and said outlet positioned to receive gas flowing through said valve when said valve is open, said compartment space communicating with said outlet;
 (c) a diaphragm on the opposite side of said compartment space from said valve, said diaphragm movable in response to a reduction in pressure in said compartment space to reduce the size of said compartment space;
 (d) one or more cam members engaged to said diaphragm and movable in response to movement of said diaphragm, movement of said cam members in response to a reduction in pressure causing axial movement of said valve to an open position permitting flow of gas from said inlet, to said compartment space and to said outlet;
 (e) a seal mounted on said valve for closing said first passageway;
 (f) a valve housing axially spaced from said seal encircling a portion of said valve, said valve housing having an axial passageway between said first chamber and atmosphere, said axial passageway being substantially the same size as said first passageway, said valve including reduced size extension slidably engaged in said axial passageway; and
 (g) a spring yieldingly urging said valve axially to a position at which said seal closes the passageway between said first chamber and said second chamber.

19. The single stage regulator according to claim 18 further including a valve guide positioned in said valve housing and encircling said valve extension.

20. The single stage regulator according to claim 18 wherein said diaphragm includes a flexible elastomeric member and a metal plate engaged thereto, said metal plate being positioned to be contacted by said one or more cam members, said cam members sliding against said plate in response to movement of said diaphragm.

21. The single stage regulator according to claim 18 further including an actuator pin contacting said valve seal, said actuator pin movable axially in response to movement of said one or more cam members to move said seal and said valve to open said first passageway to the flow of gas.

22. The single stage regulator according to claim 21 further including an adjustment member on said actuator pin for varying the amount of pressure required to move said actuator pin and valve.

23. The single stage regulator according to claim 21 wherein said body upper end is spaced from and facing said diaphragm, said upper end defining one side of said compartment space and having an elongated recess passing through said axis and overlying said valve and further including a loading lever positioned in said recess in contact with said actuator pin, said loading lever being movable by said one or more cam members to move said valve to said open position.

24. The single stage regulator according to claim 23 further including an adjustment member threadably engaged to said loading lever to vary the amount of diaphragm travel required to move said actuator pin.

25. The single stage regulator according to claim 23 wherein two cam members are pivotally mounted in opposite ends of said recess and are engaged at said ends by said loading lever.

* * * * *